United States Patent [19]

Suzuki et al.

[11] Patent Number: 4,816,408

[45] Date of Patent: Mar. 28, 1989

[54] NOZZLE DEVICE IN AN APPARATUS FOR BIOCHEMICAL REACTIONS

[75] Inventors: Hideo Suzuki, Yamato; Shuji Iwasaki, Machida; Satoru Kamada, Yamato; Yuji Higo, Nagoya, all of Japan

[73] Assignee: Toyo Soda Manufacturing Co., Ltd., Shinnanyo, Japan

[21] Appl. No.: 52,069

[22] Filed: May 21, 1987

[30] Foreign Application Priority Data

May 21, 1986 [JP] Japan ................................ 61-117111

Jul. 4, 1986 [JP] Japan ................................ 61-157607

[51] Int. Cl.[4] ......................... C12M 1/12; B01L 11/00

[52] U.S. Cl. ..................................... 435/311; 435/287; 435/291; 435/292; 422/101

[58] Field of Search ................ 435/311, 284, 286, 287, 435/291, 294, 288, 292; 422/101, 100; 436/180

[56] References Cited

U.S. PATENT DOCUMENTS

| | | | |
|---|---|---|---|
| 3,846,077 | 11/1974 | Ohringer | 422/101 X |
| 4,212,845 | 7/1980 | Stelling et al. | 422/101 |
| 4,321,327 | 3/1982 | Chen et al. | 435/288 X |
| 4,586,546 | 5/1986 | Mezei et al. | 422/100 X |
| 4,590,165 | 5/1986 | Gilles et al. | 422/100 X |
| 4,635,665 | 1/1987 | Namba et al. | 422/100 X |
| 4,644,807 | 2/1987 | Mar | 422/100 X |
| 4,699,884 | 10/1987 | Noss et al. | 435/294 X |

*Primary Examiner*—Larry Jones

*Attorney, Agent, or Firm*—Oblon, Fisher, Spivak, McClelland & Maier

[57] ABSTRACT

A nozzle device in an apparatus for biochemical reaction, including a biochemical reaction chamber, includes a nozzle having a tip and a porous filter fixed to the tip. The nozzle further includes an outer nozzle tube defining a first bore extending to the tip, a second bore extending through the porous filter and being coaxial with the first bore, an inner tube extending through the first bore to the tip and defining a third bore, the inner tube being tightly fitted into, and extending through, the second bore and having an outer diameter smaller than that of the inner diameter of the first bore to define an annular space in communication with the filter. The third bore is connected to a source of liquid and the annular space is connected with a source of suction, so that a liquid can be discharged to the reaction chamber from the first bore and sucked out of the reaction chamber through the filter.

9 Claims, 5 Drawing Sheets

NOZZLE DEVICE IN AN APPARATUS FOR BIOCHEMICAL REACTIONS

BACKGROUND OF THE INVENTION

1. Field of the Invention

The present invention relates to a nozzle device for exhausting a washing liquid in a reaction chamber and is suitably employed for biochemical reactions such as immunological reactions, particularly suitable as a B/F separation device in immunological reactions.

2. Background of the Related Art

In most apparatuses for biochemical reactions so far employed, a particular reaction is carried out in a vessel which provides a reaction chamber (cell), the inside of the reaction chamber is washed, and then the product is measured by means of a particular optical or other method.

Among these methods, for example, estimation of the enzymatic immunity may be conducted by several processes as described, for example, in Clinical Chemistry, Vol. 22, No. 8, 1243-1255 (1976). It is a commonly known process, in the competition or sandwich method known as an enzymatic immunological reaction, that an antigen-antibody reaction is carried out in a reaction chamber and the change produced on the substrate by the action of a label enzyme on the conjugate which is connected to the antigen-antibody reaction product complex is optically detected. In this process, however, it is required to leave the labelled conjugate connected to the antigen-antibody reaction product complex in the reaction chamber prior to the injection of the mentioned substrate. For this purpose, the conjugate connected to the antigen-antibody reaction product complex should be fixed in the reaction chamber, while the conjugate which is not connected to the antigen-antibody reaction product complex should be removed from the reaction chamber by washing. Leaving the conjugate which is connected to the antigen-antibody reaction product complex in the reaction chamber can usually be accomplished by a prior treatment in which one of the components that compose the antigen-antibody reaction product complex, either the antigen or the antibody, is fixed and held beforehand on an insoluble carrier in the reaction chamber (the carrier is, for example, the inner wall of the vessel which forms the reaction chamber or any granular matter packed in the reaction chamber).

The granular matter (hereinafter designated as beads), assuming it contains a magnetic substance, has an oscillating magnetic field applied from outside and oscillates in the reaction chamber which effectively agitates a sample solution and the substrate injected into the reaction chamber.

As mentioned above, the beads conveniently provide an insoluble carrier surface on which a particular antibody (or antigen) is fixed and held. For example, a particular antibody (or antigen) which corresponds to an item of inspection is fixed onto the surface of beads as an insoluble carrier and the beads are placed in a sealed test cup with which to test unknown samples. Different kinds of beads carrying different kinds of antigens fixed on them corresponding to different items of inspection are prepared and are placed in different test cups. In actual use, a suitable test cup is selected according to the object sample and the necessary item of inspection and is settled on the predetermined holding mechanism in order to bring the cup to the measuring device. Thus, an efficient procedure of measurement can be realized.

This system characteristically enables one to achieve effective results in an apparatus in which the estimation is automated.

When granular matter or beads are used as the carrier, as mentioned above, it is necessary when supplying and exhausting a washing liquid to take care that the beads are not swept away with the washing liquid current and that the current does not negatively influence on the beads.

SUMMARY OF THE INVENTION

The present invention has as its object a nozzle device with which a washing liquid supplied to the reaction chamber containing beads does not sweep away the beads when exhausted and the exhausting of the washing liquid is performed without negative influence such as that of an antigen-antibody reaction product complex combined and fixed on the surface of beads being removed from the surface. Another object is to provide a nozzle device by use of which a washing liquid does not remain unswept at a corner of the chamber or in small gaps between beads.

The nozzle device of the present invention to be applied to an apparatus for biochemical reactions which has been accomplished to carry out the above mentioned objects includes a nozzle, the tip of which may be fittingly inserted into a reaction chamber for biochemical reactions for supplying and withdrawing a liquid, and a filter installed at the tip of the nozzle, the filter having a porous structure with a number of pores for sucking a liquid.

The nozzle device of the present invention which is constructed to perform the simultaneous supply and exhaust of a washing liquid for washing the inside of a vessel containing beads comprises an outer tube with an axial hole or first bore opening toward said reaction chamber, which is movable toward the reaction chamber, a porous filter fixed at the tip of said outer tube with an axial hole or second bore of a small diameter extending therethrough, the second bore being coaxial with the first bore, and a flat surface at the outer end which can be inserted into the reaction chamber, and an inner tube installed coaxially through the first and second bores and extending down to the tip opening of the porous filter and being fit to the second bore of the porous filter substantially tightly but leaving an annular space with respect to the first bore, the inside of said inner tube defining a third bore comprising supply route of a washing liquid and the filter and annular space comprising an exhaust route of the washing liquid. The porous filter is formed from substantially rigid material or an elastic material harder than that of the inner tube.

For beads to pack the reaction chamber mentioned above, beads made from a synthetic resin are preferably used on the surface of which is fixed a particular antibody (or antigen). In addition, a magnetic substance may be included in the beads. Thus, when an oscillating magnetic field is applied from outside, the beads are oscillated in a synchronous manner to effect agitation in the reaction chamber.

The reaction chamber which is formed by said test cup or an other multititer plate is usually of a small capacity less than several milliliters and is made of a transparent or opaque synthetic resin of an appropriate material.

Beads to pack said reaction chamber are usually of a dimension of 1–2 mm in diameter which, however, depends on the capacity of reaction chamber, but those of 1.2–1.8 mm in diameter are preferred.

Porous filters are preferably selected, for example, from sintered metals, hard and soft plastics, glasses, and ceramics.

In the nozzle device of the present invention, the nozzle has a double tube structure with the inner and the outer tubes. A washing liquid is supplied through the third bore in the inside of the inner tube and the used wash liquid is exhausted through the first bore (or through the annular space between the inner tube and the first bore).

A porous filter with a flat bottom is fixed at the opening of the outer tube (first bore) from which an exhaust liquid flows into the outer tube. The porous filter prevents the beads in the reaction chamber from entering the exhaust line when the liquid is sucked for exhausting. The flat end plane of the filter serves to prevent strong pressure being applied against beads which are brought into contact with the filter. In other words, the filter should have no sharp edge, so as not to mar the beads.

The outer diameter of the porous filter should preferably be 50–90% of the inner diameter of the base of the vessel, so that every drop of the washing liquid can be drained from the corners of vessel and from the gaps between beads.

The material employed to prepare the outer and inner tubes and the porous filter of the present invention should be chemically stable with respect to the washing liquid and reaction solutions to be used, and further should be chemically so inert as not to dissolve any substance which might influence the measurement of chemical reactions of said immunity reactions.

To assure a sufficient supply of a washing liquid to the vessel, the inner tube should be inserted to extend up to the opening at the farther end of the penetrating hole (second bore) in the porous filter (either by making a concave surface at the end of the filter hole or by setting the end of the inner tube slightly recessed from the outer surface of the filter). If the end of the inner tube does not extend to the outer surface of the porous filter, a washing liquid may be partly delivered through the filter. For the same reason, the inner tube preferably fits into the penetrating hole (second bore) in the porous filter without forming a gap between them. But the presence of gap may be compensated for if the inner tube is so formed as to fit into the hole in the filter by the pressure applied on supplying a washing liquid.

In case of a double tube structure in a nozzle device with inner and outer tubes, the porous filter should be made of a substantially rigid material or an elastic material harder than the material of the inner tube.

Materials that are suitably employed to make the inner and the outer tubes and the porous filter of this invention include metals (especially stainless steel), plastics such as backelite, and Teflon for the tubes.

If the porous filter is made of a substantially rigid material such as sintered metal, glass, ceramics or hard plastic, the inner tube may be formed from either a rigid or an elastic material. If the porous filter is of an elastic material like soft plastic such as, for example, polyethylene, a substance softer than that of the porous filter such as an elastic Tygon may be used for the inner tube.

The hole diameter of pores of the porous filter should be small enough that the beads to be washed do not enter the hole, which is mostly 50–100 μm in diameter.

The device of the present invention can be employed preferably in an apparatus for biochemical reactions such as a measuring device for immunological reactions in which the reaction chamber in a vessel having one or more reaction chambers is packed with beads. The device may then operate as a washing device or a B/F separation device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 4:
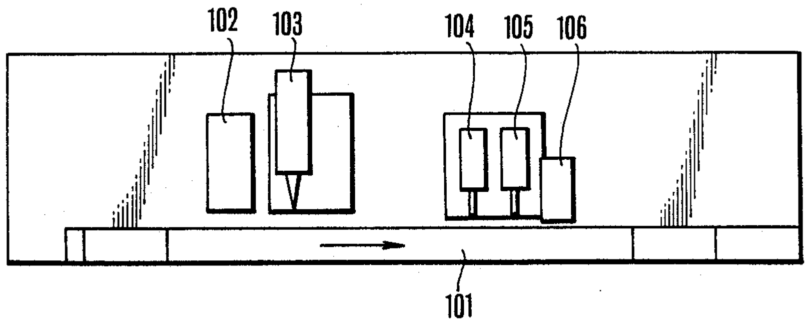
FIG. 4 is a schematic view of a measuring apparatus for enzymatic immunity in which the nozzle device of the present invention may be installed as a B/F separation device.
Figure 5:
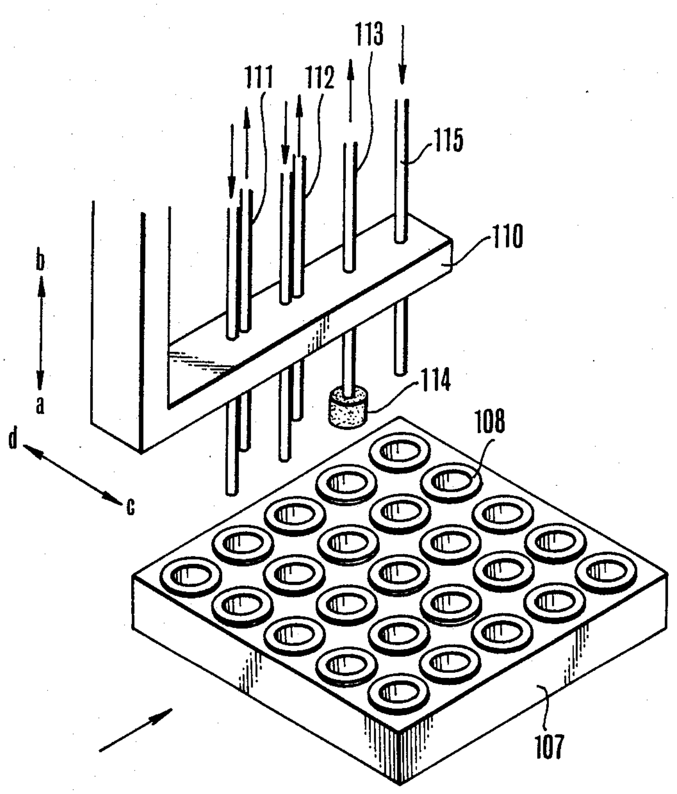
FIG. 5 is a perspective view showing a test plate carrying test cups and the transfer mechanism thereof.

In FIG. 4, the transfer route 101 transfers a test plate 107, carrying test cups 108 arranged in an array in the direction as shown by the arrow in FIG. 5. Above and in facing opposition to the transfer route are placed successively, in the order from upstream to downstream of the transfer route, seal breaker 102, sample solution injection device 103, B/F separation device 104, substrate injection device 105 and a photometric device 106.

Devices other than the B/F separation device 104, i.e., the seal breaker 102, the sample solution injection device 103, the substrate injection device 105 and the photometric device 106, work as follows. First a sealing foil of a test cup is broken at 102, then a predetermined amount of a sample solution is injected into an open reaction cell using the nozzle device 103. The B/F separation follows the subsequent reaction, after which a substrate is injected into the reaction cell, which produces an optically detectable change by the action of an enzyme labelled on an above mentioned antigen-antibody reaction product complex, and then the change produced on said substrate is detected and the intensity of the change is measured.

Figure 6:
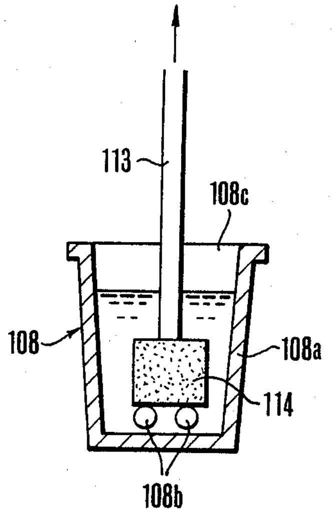
FIG. 6 is a cross section which illustrates the working detail of an embodiment of the B/F separation device.

The test cup 108 consists, as seen in FIG. 6, of a cup type vessel proper 108*a* which is upwardly open, a plurality of beads 108*b* placed in the cup proper 108*a*, and a seal which is not shown in the figure but seals the upward opening 8*c* of the cup proper 108*a*. The beads 108*b* are beforehand applied with a particular antibody (or antigen) immobilized on their surface.

The test plate 107 carries test cups 108 arranged a two dimensional array as seen in FIG. 5. Each cup is placed in a hole (not shown in the figure).

The test plate 107 is transferred by a transferring mechanism (not shown in the figure) in the direction of the arrow in FIGS. 4 and 5 along the transfer route 101.

FIG. 5 partly shows the B/F device 104 and the substrate injection device 105. In this example these parts are mounted on a single frame 110 so that washing, the B/F separation and the injection of the substrate may be successively performed.

More particularly, in FIG. 5, both 111 and 112 are respectively washing nozzles composed of a pair of tubes for supply and exhaust of a washing liquid to assure thorough washing in a double step treatment, as a part of a B/F device 104. Element 113 is an exhaust tube for a liquid from the B/F device where a filter 114 is attached to the tip, while 115 is a nozzle for the substrate injection device 105. The frame 110 with the nozzles mounted on it can be moved in the vertical (a-b) and scanning (c-d) directions by a driving mechanism (not shown in the Figures). By movement of the frame 110 in the a-direction, the nozzles are inserted into corresponding cups and washing, B/F separation and the substrate injection are performed, after which the frame returns to the upper position by movement in the b-direction. Then the frame 110 moves by a small predetermined distance in the c-direction to face an adjacent line of test cups and the same procedure as above is repeated.

The end of the exhaust tube 113 of the B/F device mentioned above is connected to a suction tank (not shown in the Figure) to completely suck and exhaust the liquid in the test cup 108.

Figure 7A:
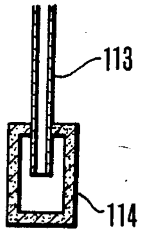
FIG. 7(*a*) and FIG. (*b*) show structures of other filters.
Figure 7B:
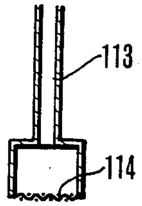

FIG. 6 illustrates the action of the B/F separation device. The tube 113 is lowered into a test cup 108 until the filter 114 at the tip touches beads 108*b* in the cup and suction is performed at this position. By using a soft or flexible material in making the filter 114, the level of suction reaches to a depth comparable to the bottom of beads in the cup. FIG. 7(*a*) and (*b*) show other configurations of a liquid exhaust tube of the B/F separation device 104. The filter at the tip may be either a block or a membrane. In most cases, the filter preferably covers 70–80% of the base area of a reaction cell involved.

Utilizing the B/F device thus formed, changes in a substrate as a measure of enzymatic immunity reaction can be detected and estimated with a high accuracy regarding the activity of an enzyme which is labelled on the surface of beads in the combined state with an antigen-antibody reaction product complex.

Figure 1:
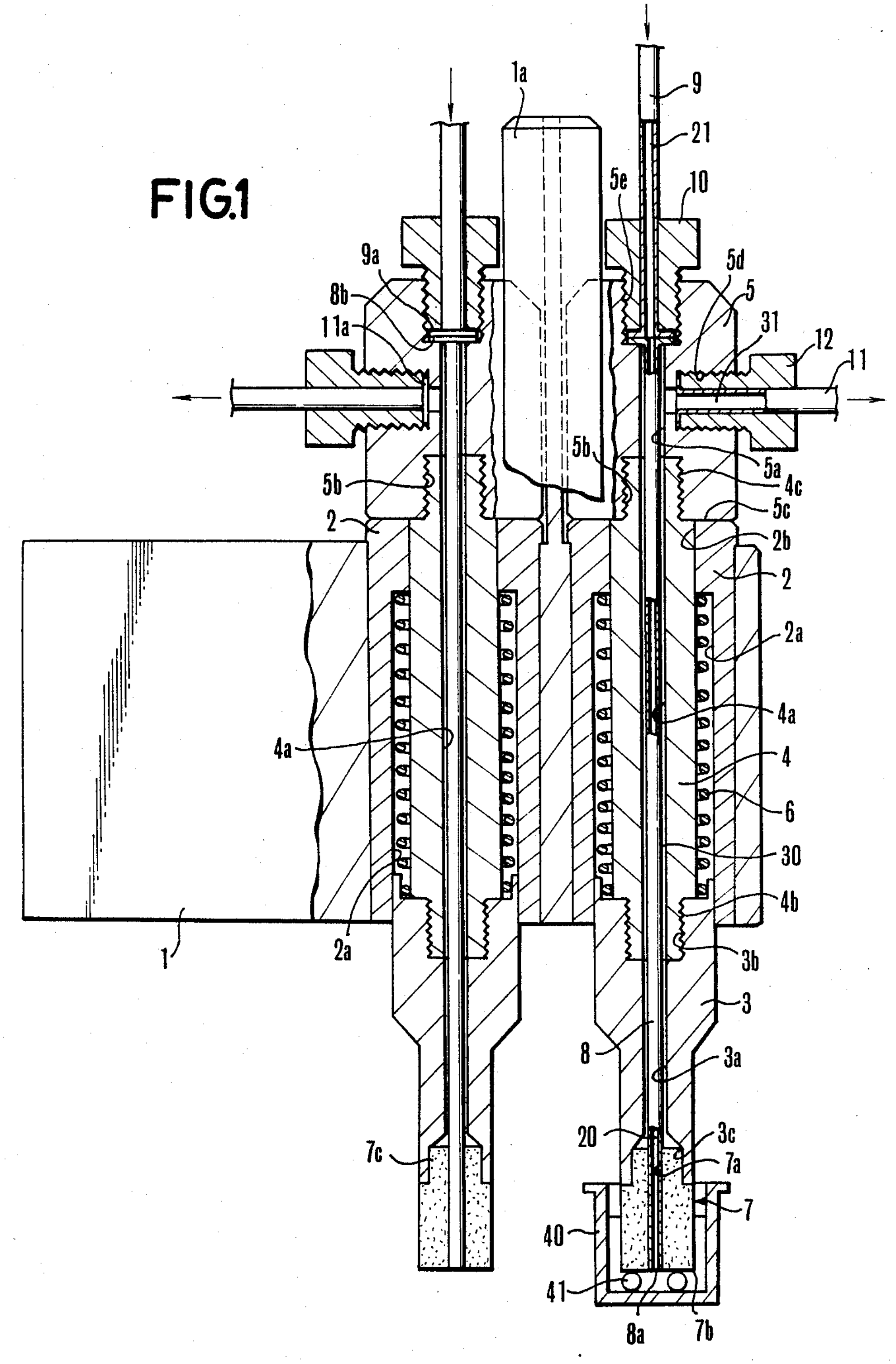
FIG. 1 shows an example of a construction, partly in section, and in a front view.
Figure 2:
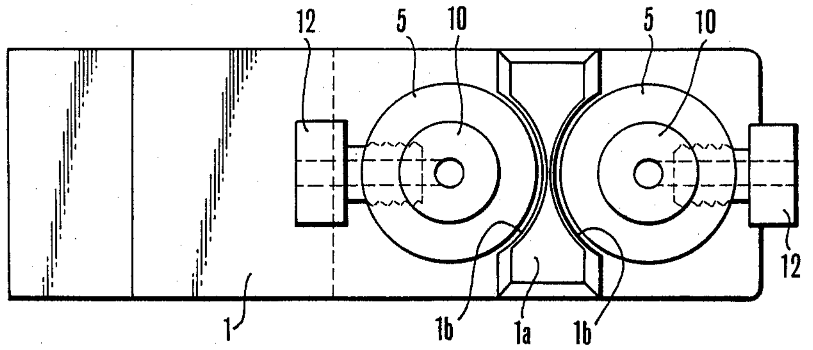
FIG. 2 is a plan view of the nozzle device.
Figure 3A:
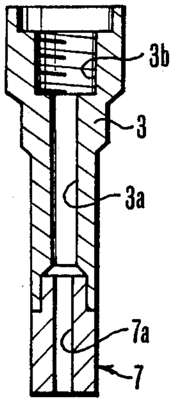
FIGS. 3(*a*) to (*c*) respectively, show front sectional, bottom and top views of the first part of the outer tube of the nozzle of the nozzle device.
Figure 3B:
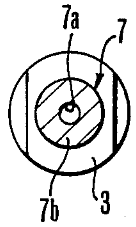
Figure 3C:
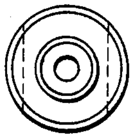

In a particularly advantageous emodiment, each of the pair of working nozzles 111 or 112 of the B/F device is formed by coaxial inner and outer nozzles as shown in FIGS. 1–3. The nozzles of FIGS. 1–3 may also be used for B/F separation to replace nozzle 113.

FIGS. 1 to 3 show a twin nozzle device which is an embodiment of this invention. A pair of nozzles are mounted on a supporting frame 1 (corresponds to frame 110) and are of the same structure except that they can be fixed to the frame independently of each other.

The supporting frame 1 is movable within a limited range in the vertical direction by means of a mechanism not shown in the figure. The mechanism operates to insert the lower end of the nozzle into a reaction chamber 40 (corresponds to cup 8) and withdraw the same from the reaction chamber, as will be described later.

The sleeve 2 supporting each nozzle is a cylinder with both ends open and fixed to the supporting frame 1. The cylinder is hollowed in two different diameters as seen in FIG. 1. The part 2*a* with a larger inner diameter accommodates a buffering spring 6. The part 2*b* with a smaller inner diameter, together with the part 2*a* with a larger inner diameter, supports and guides the sliding movement of a respective outer nozzle tube 3, 4 and 5 which moves in the vertical direction. Parts of each outer nozzle tube 3, 4 and 5 are explained in detail below.

Each nozzle of this example is a unit composed of three components, that is the outer nozzle tube 3, 4 and 5 as mentioned above, a porous filter 7 fixed to the lower end of outer nozzle tube, and an inner nozzle tube 8 which is installed through the inside of the outer nozzle tube and the porous filter 7 so that the three components have an axis in common. Details are given in the following explanation.

The first explanation will be of the outer nozzle tube. The outer nozzle tube, as a unit formed from three components, not only forms a partial structure of the nozzle which is supported by the frame 1 that supports the nozzle, but also provides an exhaust route for a washing liquid so that the liquid flows along the axial direction.

The first part 3 of the outer nozzle tube is the lower part of the outer nozzle tube and is made of bakelite. An axial hole 3*a* penetrates the tube in the vertical direction and a wider opening at the lower end forms a part 3*c* which accommodates a press fitted filter 7. A female screw socket 3*b* is provided at the top end of part 3 which enables screw threading with the part 2 described below.

The second part 4 of the outer nozzle tube forms the middle portion of the outer nozzle tube and is made of stainless steel, whose axial hole 4*a* penetrates in the vertical direction, and there is a male screw socket 4*b* at the lower end for screw threading with the first part 3 described above. A male screw socket 4*c* is provided at the top of part 4 which serves to connect by screwing with the third part described below. The second part 4 itself is supported by the sleeve 2 in such a manner as to permit movement in the vertical direction.

The third part 5 of the outer nozzle tube forms the upper portion of the outer nozzle tube and is made of stainless steel. An axial hole 5*a* penetrates the third part 5 in the vertical direction. The axial holes 3*a*, 4*a* and 5*a* together define a first bore. There is a female screw socket 5*b* at the lower end for screw threading with the second part 4. The lower end of the third part 5 forms a plane which comes into contact with the upper plane of the sleeve 2 supporting the nozzle. Thus, the upper plane of the sleeve 2 forms a stopper plane 5*c* or stop means which limits the downward movement of the outer nozzle tube.

An inner tube 8 extends through the axial holes 3*a*, 4*a* and 5*a* to define a supply line 20 (third bore), as a liquid delivery means for a washing liquid. The inner tube 8 has an outer diameter such that an annular space remains between the inner tube 8 and the walls of the axial holes, thereby forming an exhaust line 30 for a washing liquid.

The third part 5 is provided with two connecting parts; one connects the exhaust line 30 for a washing liquid with an external exhaust pipe 11.

Next the porous filter of this embodiment will be explained. The porous filter 7 is formed in the shape of a cylinder press fitted into the end of the outer tube and has an axial hole *7a* extending through it to define a second bore. The front of the porous filter 7 forms a circular plane *7b* of a diameter of 6 mm such that the filter may be introduced into a reaction vessel 40 having a base with an inner diameter of, for example, 8 mm ϕ, without scraping the reaction vessel. For the same reason, the edge of the front plane *7b* is preferably made smooth. The part *7c* of the filter is conveniently shaped for easy and secure installment into the tip of the first part 3 of the outer tube.

The hole *7a* penetrating the porous filter of this example should have an inner diameter which is large enough as to fittingly accommodate the inner tube 8 of the nozzle. Usually an inner diameter 1.0–2.0 mm is sufficient.

While maintaining the configuration as mentioned above, the frame 1 supporting the nozzle can be lowered by a mechanism not shown in the figures. The nozzle is simultaneously lowered while maintaining the configuration as shown in the figures. If the movement of the frame 1 supporting the nozzle were to be stopped as soon as the lower end of the nozzle hits a hard body, it would be possible to bring the nozzle to the desired position. In an actual operation, however, control with such precision is difficult to achieve. In this embodiment, the problem is solved by using the buffering spring 6 as mentioned above. In other words, the nozzle (or the outer tube of the nozzle in this embodiment) is so constructed as to absorb an upward thrust on the nozzle by the buffering spring 6, as well as to make the nozzle movable in the up and down direction. Thus, the nozzle can be protected from breakage on collision with a hard body.

In this embodiment, as has been described above, the first part 3 of the outer tube of the nozzle is composed of bakelite, while the second and the third parts 4 and 5, which do not make direct contact with the reaction vessel but only with the exhaust route of a washing liquid, may be made of a stainless steel material. Thus, the requirements with regard to the chemical stability and mechanical strength can be met.

As has been described in detail, the nozzle device of the present invention enables exhausting of a liquid and supplying and exhausting of a washing liquid from a reaction chamber containing beads to be performed without a loss of beads being ejected to the outside of the vessel and a loss of antigen-antibody reaction product complex held on the surface of the beads, thus evidencing a remarkable effect.

Another remarkable effect of this invention is that the nozzle device of this invention can completely suck a washing liquid without leaving drops of the liquid at a corner of vessel or behind the beads.

Obviously, numerous modifications and variations of the present invention are possible in light of the above teachings. It is therefore to be understood that within the scope of the appended claims, the invention may be practiced otherwise than as specifically described herein.

The inner tube 8 of the nozzle is manufactured from PTFE (polytetrafluoroethylene) which is installed in such a manner that the tip *8a* extends through the hole *7a* penetrating the porous filter 7 down to the lower end plane *7b* and, as described above, the tube 8 does not contact the outer tubes 3, 4 and 5 leaving the annular exhaust line 30 inbetween. The inner tube 8 is connected at the uppermost end to the outer pipe 9 which supplies a washing liquid as mentioned before. The diameter of the exhaust route 30 may be designed in accordance with the amount of washing liquids necessary for the apparatus.

Using the nozzle device constructed as described above, a washing liquid can be supplied and exhausted to perform washing as follows: with the frame 1 supporting the nozzle stationed at a high position, a washing liquid is supplied through the supply route 20 in the inside of the inner tube 8, and then the frame 1 is lowered to insert the porous filter 7 at the lower end of the nozzle into a vessel 40. The washing liquid is exhausted through the porous filter 7 and the exhaust route 30, as a liquid exhaust means while the porous filter gently presses the beads 41 at the front plane 76.

As has been described in detail, the nozzle device of the present invention enables exhausting of a liquid and supplying and exhausting of a washing liquid from a reaction chamber containing beads to be performed without a loss of beads being ejected to the outside of the vessel and a loss of antigen-antibody reaction product complex held on the surface of the beads, thus evidencing a remarkable effect.

Another remarkable effect of this invention is that the nozzle device of this invention can completely suck a washing liquid without leaving drops of the liquid at a corner of vessel or behind the beads.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A nozzle device in an apparatus for biochemical reactions, including a biochemical reaction chamber, comprising:

a nozzle having a tip, means for delivery of a liquid to said tip and means for exhaust of a liquid from said tip;

a porous filter fixed to said tip; and means for inserting said filter into said reaction chamber, wherein said nozzle comprises:

an outer nozzle tube defining a first bore extending to said tip;

a second bore extending through said porous filter and being coaxial with said first bore;

an inner tube extending through said first bore to said tip and defining a third bore, said inner tube being tightly fitted into, and extending through said second bore and having an outer diameter smaller than an inner diameter of said first bore to define an annular space in communication with said filter;

means for connecting said third bore of said inner tube with a source of liquid, whereby said third bore comprises said liquid delivery means; and means for connecting said annular space with a source of suction, whereby said filter and said annular space comprise said liquid exhaust means.

2. The nozzle device of claim 1 including granular beads in said reaction chamber, said granular beads having surfaces capable of supporting an antigen-antibody reaction product complex.

3. The nozzle device of claim 1, wherein said nozzle device comprises a B/F separation means of said biochemical reaction apparatus, wherein said means for exhaust of a liquid comprise suction means capable of sucking a washing liquid from said reaction chamber.

4. The nozzle device of claim 1, wherein said filter has a flat surface at an end opposite said tip.

5. The nozzle device of claim 4, wherein said filter is formed of a rigid material.

6. The nozzle of claim 4, wherein said filter is formed of an elastic material harder than that of said inner tube.

7. The nozzle of claim 1, including granular beads in said reaction chamber, said granular beads having surfaces capable of supporting an antigen-antibody reaction product complex.

8. The nozzle of claim 7, wherein said nozzle device comprises a washing liquid supply and exhaust means of said biochemical reaction apparatus.

9. The nozzle of claim 8, wherein said means for inserting comprise:

a movable supporting frame having at least one sleeve;

one of said nozzles mounted in each said sleeve for vertical movement;

means for biasing each said nozzle downwards; and stop means for limiting a downward movement of each said nozzle, whereby contact between said filter and said beads in said reaction chamber causes each said nozzle to lift off said stop means in opposition to said biasing means.

* * * * *